United States Patent [19]
Highsmith et al.

[11] Patent Number: 5,451,682
[45] Date of Patent: Sep. 19, 1995

[54] METHOD FOR SYNTHESIZING 5-AMINOTETRAZOLE

[75] Inventors: Thomas K. Highsmith, North Ogden; Gary K. Lund, Ogden, both of Utah

[73] Assignee: Thiokol Corporation, Ogden, Utah

[21] Appl. No.: 179,559

[22] Filed: Jan. 10, 1994

[51] Int. Cl.$^6$ ........................................... C07D 257/06
[52] U.S. Cl. ....................................................... 548/251
[58] Field of Search ......................................... 548/251

[56] References Cited

U.S. PATENT DOCUMENTS

| | | | |
|---|---|---|---|
| 3,171,249 | 2/1965 | Bell | 548/251 |
| 3,235,558 | 2/1966 | Harrison et al. | 548/251 |
| 3,468,730 | 9/1969 | Gawlick et al. | 149/61 |
| 3,557,285 | 1/1971 | Enkoji et al. | 548/251 |
| 3,719,604 | 3/1973 | Prior et al. | 252/186 |
| 3,739,574 | 6/1973 | Godfrey | 60/39.03 |
| 3,778,084 | 12/1973 | Sutherland et al. | 280/150 AB |
| 3,898,112 | 8/1975 | Strecker et al. | 149/19.9 |
| 4,142,029 | 2/1979 | Illy | 521/95 |
| 4,608,102 | 8/1986 | Krampen et al. | 149/92 |
| 4,909,549 | 3/1990 | Poole et al. | 280/738 |
| 4,948,439 | 8/1990 | Poole et al. | 149/46 |
| 5,035,757 | 7/1991 | Poole | 149/46 |
| 5,084,118 | 1/1992 | Poole | 149/22 |
| 5,139,588 | 8/1992 | Poole | 149/61 |
| 5,197,758 | 3/1993 | Lund et al. | 280/741 |

FOREIGN PATENT DOCUMENTS

| | | | |
|---|---|---|---|
| 0519485A1 | 12/1992 | European Pat. Off. | C06D 5/60 |
| 426343 | 3/1926 | Germany | 548/251 |
| 285080 | 4/1929 | United Kingdom | 548/251 |

OTHER PUBLICATIONS

Frankel et al., "Derivatives of Dicyanamide," *Jo. Org. Chem.*, vol. 28, pp. 2428–2431, Sep. 1963.

Lieber et al., "The Reaction of Nitrous Acid with Nitroaminoguanidine," *J. Am. Chem. Soc.*, vol. 73, pp. 2327–2329, May 1951.

Lieber et al., "The Ultraviolet Absorption Spectra of 5-Nitroaminotetrazole and its Salts," *J. Am. Chem. Soc.*, vol. 73, pp. 2329–2331, May 1951.

Lieber et al., "The Comparative Acidic Properties of Some 5-Substituted Tetrazoles," *J. Am. Chem. Soc.*, vol. 73, pp. 1792–1795, Apr. 1951.

G. C. Chiang, "Preparation of 2-aminotriazine herbicide intermediates via metal dicyanimide ligand complexes," *Chemical Abstracts*, vol. 113, No. 231414f, p. 728, 1990.

Nakamura, et al., "Preparation of calcium dicyanamide aqueous solution as a pharmaceutical starting material," *Chemical Abstracts*, vol. 109, No. 148873b, p. 671, 1988.

Nakamura, et al., "A process for the preparation of dicyanamide metal salts as intermediates for antimicrobials," *Chemical Abstracts*, vol. 109, No. 210568m, p. 618, 1988.

W. P. Norris and R. A. Henry, "Cyanoguanyl Azide Chemistry," pp. 650–660, Mar. 1964.

M. Kuhn and R. Mecke, "IR-Spektroskopische Untersuchungen am Dicyanamid-Anion," *Chem. Ber.*, vol. 94, pp. 3010–3015, 1961.

Joseph S. Mihina, et al., "The Reaction of Nitriles With Hydrazoic Acid: Synthesis of Monosubstituted Tetrazoles," Kedzie Chemical Lab., pp. 1082–1092, Apr. 1950.

R. Stollé, "5-Aminotetrazole," *Chemical Abstracts, 10-Organic Chemistry*, vol. 23, p. 4471, 1929.

R. Stollé et al., "Zur Kenntnis des Amino-5-tetrazols," *Chem. Ber.*, vol. 62, pp. 1118–1127, 1929.

William L. Burdick, "Some Ammono-Carbonic Acids and Their Reactions in Liquid Ammonia," *The Journal of the American Chemical Society*, vol. 47, No. 6, pp. 1485–1491, Jun. 1925.

The Merck Index 9th Ed Merck & Co Rahway, N.J. (1976).

*Primary Examiner*—David B. Springer
*Attorney, Agent, or Firm*—Ronald L. Lyons; Madson & Metcalf

[57] ABSTRACT

A process of preparing 5-aminotetrazole ("5-AT") which proceeds at substantially neutral pH is disclosed. In the process, cyanamide or dicyandiamide and an azide salt are reacted at elevated temperature in the presence of an acid reagent. The acid reagent has a $pK_a$ in the range from about 3 to about 7. Large quantities of hydrazoic acid are not produced during the reaction. Upon completion of the reaction, the reaction mixture is acidified to a pH less than 3 to protonate the 5-AT. Several variations of the acidification step permit control of particle size and morphology. The precipitated particles are isolated to yield 5-AT.

46 Claims, No Drawings

METHOD FOR SYNTHESIZING 5-AMINOTETRAZOLE

FIELD OF THE INVENTION

The present invention relates to an improved method of synthesizing 5-aminotetrazole and salts thereof. More particularly, the process of the present invention rapidly produces 5-aminotetrazole under neutral conditions and minimizes the formation of undesirable hydrazoic acid.

BACKGROUND OF INVENTION

A method of synthesizing 5-aminotetrazole (hereinafter referred to as "5-AT") is described by R. Stolléet al., "Zur Kenntnis des Amino-5-terazols," *Chem. Ber.*, vol 62, pp.1118–26, (1929). According to the procedure of Stollé, 5-AT is obtained by reacting aqueous hydrazoic acid ($HN_3$) and dicyandiamide ($NH_2C(NH)NHCN$). A significant disadvantage of Stollé's procedure is the need for initial large quantities of hydrazoic acid. Hydrazoic acid is highly explosive and is also a potent vasodilator which can adversely affect the health of workers exposed to it.

More recently, Joseph S. Mihina and Robert M. Herbst, "The Reaction of Nitriles with Hydrazoic Acid: Synthesis of Monosubstituted Tetrazoles," *Journal of Organic Chemistry*, pp. 1082–92, (1950), discloses a variation of Stollé's procedure. According to Mihina et al., a suspension of dicyandiamide and sodium azide was heated to 65° C. Concentrated hydrochloric acid was added in small portions with frequent manual agitation. After complete addition of the acid, the mixture was kept at 65°–70° C. for 6 hours during which the product began to crystallize. The semi-solid mass was allowed to stand overnight and was chilled thoroughly before being filtered and washed with ice water. Although the Mihina et al. procedure avoids producing initially large quantities of hydrazoic acid by adding the hydrochloric acid in small portions over time, hydrazoic acid is still, nevertheless, produced and the procedure is cumbersome and protracted.

It will be appreciated that it would be a significant advancement in the art to provide rapid, simple processes for synthesizing 5-AT which do not require or produce large quantities of hydrazoic acid.

Such processes for preparing 5-AT are disclosed and claimed herein.

SUMMARY OF THE INVENTION

The present invention is directed to a method of synthesizing 5-aminotetrazole ("5-AT"). The reaction for preparing 5-AT is shown below:

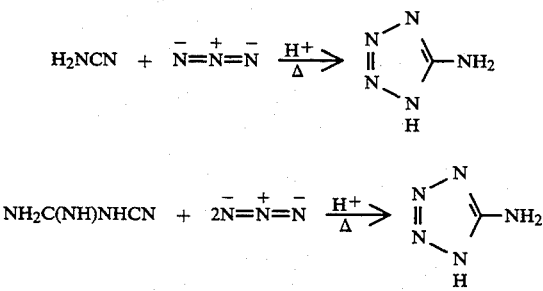

In the process according to the present invention, cyanamide or dicyandiamide is reacted with an azide salt and an acid reagent. Although the azide salt can be used in a stoichiometric excess, it is currently preferred to avoid excess azide to suppress $HN_3$ formation. Thus, it is currently preferred to use a molar excess of the cyanamide or dicyandiamide. As used herein, dicyandiamide provides results substantially equivalent to cyanamide. The major difference is that dicyanamide requires approximately two chemical equivalents of azide to complete the reaction. It is currently preferred that a stoichiometric excess acid is used.

It has been found that the reaction proceeds best when the acid reagent has a $pK_a$ in the range from about 3 to about 7, and preferably from 3 to about 5. The acid reagent is preferably soluble at reaction conditions, and subsequently at low temperature and low pH. In addition, the acid reagent should not participate or interfere with the reaction, that is, the acid reagent should not react with the azide or cyanamide reactants. Suitable inorganic and organic acids may be used. Acid reagents which may be used in the present invention include boric acid, ammonium chloride, amine hydrochlorides, and monosodium or monopotassium phosphate. Boric acid is a particularly preferred acid reagent.

The reaction solution is heated to a temperature greater than 75° C., and preferably at reflux temperature. The reaction ingredients may be combined either prior to or during the heating step. After the reaction is substantially complete, the reaction solution is acidified to protonate the 5-AT, and the 5-AT product is isolated, preferably by filtering and washing with water.

Several variations of the acidification step are possible. For example, acid may be introduced into the reaction solution by direct addition or the reaction solution may be introduced into the acid by indirect addition. It is generally preferred that acid and reaction solution be agitated during the acidification step. Generally, sufficient acid is used in the acidifying step to lower the reaction solution's pH to a value of 3 or below. Thus, the acid used to acidify the reaction solution preferably has a $pK_a < 3$, and more preferably a $pK_a < 1$. The acid is also preferably soluble in the reaction solution at the pH range and temperature of the reaction. Inorganic and organic acids may be used in the acidification step. Currently preferred acids include $HCl$, $H_2SO_4$, $H_3PO_4$, $HNO_3$, $Cl_2CCO_2H$, $Cl_3CCO_2H$, $F_3CCO_2H$, $HCO_2H$, $HClO_4$, and mixtures thereof.

DETAILED DESCRIPTION OF THE INVENTION

In the process of the present invention cyanamide or dicyandiamide and an azide salt are reacted in the presence of an acid reagent. The reaction preferably takes place at a temperature in the range from about 75° C. to reflux temperature. After the reaction is substantially complete, the reaction solution is acidified to protonate the 5-AT, and the product is isolated.

Approximately one mole, and preferably 1.5 mole, of the acid reagent is present for each mole of the azide salt. The reaction proceeds best when the acid reagent has a $pK_a$ in the range from about 3 to about 9, and preferably from about 3 to about 5. The acid reagent is preferably soluble at low pH and low temperature so that it remains in solution during acidification of the 5-AT. In addition, the acid reagent should not participate or interfere with the reaction, that is, it does not react with the azide salt or cyanamide under the reaction conditions. Suitable inorganic and organic acids may be used. Acid reagents which may be used in the present invention include boric acid, ammonium chloride, buffer systems based on phosphate or acetate, chloroacetic acid, acetic acid, formic acid, malic acid, malonic acid, glycolic acid, and lactic acid.

An important advantage of using an acid reagent defined herein is that the process of synthesizing 5-AT proceeds at substantially neutral pH, that is from about pH 6 to about 8. As a result, dangerous quantities of hydrazoic acid are never present during the reaction process.

The reaction solution is heated, such as to a temperature greater than 75° C., and preferably at reflux temperature. The reflux temperature will vary depending on the ingredient concentrations and upon the local elevation or barometric pressure. The reflux temperature will generally be greater than 90° C. It is possible to increase the reflux temperature by applying pressure to the reaction. It has been observed that yields improve as the reaction temperature approaches reflux; therefore, the reaction temperature is preferably at or near the reflux temperature (greater than about 95° C.). The reaction ingredients may be combined either prior to or during the heating step.

After the reaction is substantially complete, the reaction solution is acidified to protonate the 5-AT. Acid may be introduced into the reaction solution by direct addition or the reaction solution may be introduced into the acid by indirect addition. In addition, the temperature of the reaction solution and acid may also vary from near 0° C. to reflux temperature. Rapid agitation of the solutions may help reduce particle size. The reaction solution is preferably acidified to a pH less than 3 to ensure that the 5-AT is fully protonated. Taking the solution to a low pH also improves purity by reducing the presence of salt impurities. The acid used to acidify the reaction solution preferably has a $pK_a$ <3. The acid is preferably soluble in the reaction solution at the pH range and temperature of the reaction. Inorganic and organic acids may be used in the acidification step. Currently preferred acids include HCl, $H_2SO_4$, $H_3PO_4$, $HNO_3$, $Cl_2CCO_2H$, $Cl_3CCO_2H$, $F_3CCO_2H$, $HCO_2H$, $HClO_4$, and mixtures thereof.

After acidification, the precipitated particles are isolated. Conventional particle separation techniques may be used such as centrifugation, filtration, and ultrafiltration, with filtration and washing being currently preferred. Washing removes acid and soluble by-products. Typically, the final product is washed with water until the effluent has a pH of about 4 to 6. An important advantage of the present invention is the ability to obtain pure 5-AT suitable for its intended use without further purification.

The present invention also includes the process for making inorganic salts of 5-AT. Such a process is substantially the same as the process described above, except that instead of acidifying the reaction solution in order to protonate the 5-AT, a compound having a cation capable of forming the salt of 5-AT is added. The compound can be any organic or inorganic metal salt provided that the counter ion (anion) remains in solution after the cation exchange. Thus, the inorganic 5-AT salt is formed in situ. The salt of 5-AT prepared herein can be further treated with a strong acid to obtain the protonated 5-AT.

In principle, the cationic compound added can have a metal cation of a metal from Group Ia, Ib, IIa, IIb, IIIa, IVb, VIb or VIII of the Periodic Table (Merck Index (9th Edition 1976)). Illustrative suitable metals include Bi, Ca, Cd, Hg, Mo, W, Sn, Pb, Sr, Mn, Fe, Co, Ni, Cu, Zn, Tl, Pd, Pt, Cr, Ti, Ag, Au, Ba, K, Li, and, for instance, Be. The particular metal 5-AT salt selected will be governed by various considerations such as the particular end use of the salt. For an air bag application, the salt can be selected based on the criterion that the salt-fueled gas generant composition should have a good burn rate, low hydration, low toxicity, and low particulate formation.

Such inorganic 5-AT salts can be isolated by conventional methods including centrifugation, filtration, decantation, and solvent/nonsolvent extraction. Others isolation methods will be apparent to a person skilled in the art based on disclosure herein.

The present invention is further described in the following nonlimiting examples.

EXAMPLE 1

In a 500 ml round bottom flask fitted with a magnetic stirrer, reflux condenser, and thermometer were combined with 100 ml of water, 14.7 g sodium azide and 14.7 g boric acid. To the stirred solution were added 20 g cyanamide (in a 50% aqueous solution) and the resulting solution was heated to reflux. After approximately 1.5 hours, the reaction was complete according to $^{13}C$ NMR. Without cooling the solution, 25 ml of concentrated hydrochloric acid was added slowly until the pH was roughly 1. The solution was cooled in an ice bath. The precipitate was collected by filtration and washed two times with room temperature water. The filtrate was air dried and then further dried in vacuo at room temperature, yielding 17.9 g of pure 5-AT based on $^{13}C$ NMR.

EXAMPLE 2

In a one liter single neck round bottom flask equipped with a magnetic stir bar and reflux condenser were placed 10.0 g of dicyandiamide, 7.74 g of sodium azide and 11.0 g of boric acid in 100 ml of distilled water. The solution thus obtained was brought to reflux by which time it had turned slightly orange. A small sample was taken after 2 hours and analyzed by $^{13}C$ NMR for the disappearance of the dicyandiamide, whereupon it was found that significant starting material remained. The reaction was allowed to proceed for 24 hours and then 15 ml of concentrated HCl was added while the solution was still hot. Upon cooling a white crystalline solid had formed, this was isolated by filtration and washed twice with 50 ml portions of ice cold distilled water. The solid was then dried in vacuo at 60° C. for several hours. The dried product (14.5 g, 100%) was analyzed by $^{13}C$ NMR, and found to be essentially pure 5-AT with a trace of its sodium salt, presumably resulting from incomplete acidification.

From the foregoing, it will be appreciated that the present invention provides rapid, simple processes for synthesizing 5-AT which do not require or produce large quantities of hydrazoic acid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The claimed invention is:

1. A process for preparing 5-aminotetrazole comprising the steps of:
   (a) combining cyanamide or dicyandiamide, an azide salt, and an acid reagent in water, wherein the combined ingredients form a reaction solution;
   (b) heating the reaction solution to a temperature in the range from about 75° C. to reflux temperature;
   (c) acidifying the reaction solution with a strong acid after the reaction is substantially complete to protonate the 5-aminotetrazole product; and
   (d) isolating the 5-aminotetrazole product.

2. A process for preparing 5-aminotetrazole as defined in claim 1, wherein the cyanamide or dicyandiamide, the azide salt, and the acid reagent are present at approximately stoichiometric quantities.

3. A process for preparing 5-aminotetrazole as defined in claim 1, wherein the cyanamide or dicyandiamide is present at a stoichiometric excess quantity.

4. A process for preparing 5-aminotetrazole as defined in claim 1, wherein the acid reagent is present at a stoichiometric excess quantity.

5. A process for preparing 5-aminotetrazole as defined in claim 1, wherein the reaction solution is heated to reflux temperature.

6. A process for preparing 5-aminotetrazole as defined in claim 1, wherein the reaction solution is well agitated and wherein the acidifying step is achieved by introducing the strong acid into the reaction solution.

7. A process for preparing 5-aminotetrazole as defined in claim 6, wherein the temperature of the reaction solution during the acidifying step is greater than about 0° C.

8. A process for preparing 5-aminotetrazole as defined in claim 6, wherein the reaction solution temperature during the acidifying step is at or near reflux temperature.

9. A process for preparing 5-aminotetrazole as defined in claim 6, wherein the strong acid is below room temperature.

10. A process for preparing 5-aminotetrazole as defined in claim 6, wherein sufficient strong acid is used in the acidifying step to lower the reaction solution's pH to a value of 3 or below.

11. A process for preparing 5-aminotetrazole as defined in claim 6, wherein the strong acid is an organic acid having a $pK_a < 3$.

12. A process for preparing 5-aminotetrazole as defined in claim 6, wherein the strong acid is an inorganic acid having a $pK_a < 3$.

13. A process for preparing 5-aminotetrazole as defined in claim 6, wherein the strong acid is selected from HCl, $H_2SO_4$, $H_3PO_4$, $HNO_3$, $Cl_2CCO_2H$, $Cl_3CCO_2H$, $F_3CCO_2H$, $HCO_2H$, $HClO_4$, and mixtures thereof.

14. A process for preparing 5-aminotetrazole as defined in claim 1, wherein the reaction solution is well agitated and wherein the acidifying step is achieved by introducing the reaction solution into the strong acid.

15. A process for preparing 5-aminotetrazole as defined in claim 14, wherein the temperature of the reaction solution during the acidifying step is greater than about 0° C.

16. A process for preparing 5-aminotetrazole as defined in claim 14, wherein the reaction solution temperature during the acidifying step is at or near reflux temperature.

17. A process for preparing 5-aminotetrazole as defined in claim 14, wherein the strong acid is below room temperature.

18. A process for preparing 5-aminotetrazole as defined in claim 14, wherein sufficient strong acid is used in the acidifying step to lower the reaction solution's pH to a value of 3 or below.

19. A process for preparing 5-aminotetrazole as defined in claim 14, wherein the strong acid is an organic acid having a $pK_a < 3$.

20. A process for preparing 5-aminotetrazole as defined in claim 14, wherein the strong acid is an inorganic acid having a $pK_a < 3$.

21. A process for preparing 5-aminotetrazole as defined in claim 14, wherein the strong acid is selected from HCl, $H_2SO_4$, $H_3PO_4$, $HNO_3$, $Cl_2CCO_2H$, $Cl_3CCO_2H$, $F_3CCO_2H$, $HCO_2H$, $HClO_4$, and mixtures thereof.

22. A process for preparing 5-aminotetrazole as defined in claim 1, wherein the 5-aminotetrazole product is isolated by filtering and washing.

23. A process for preparing 5-aminotetrazole as defined in claim 1, wherein the acid reagent has a $pK_a$ in the range from about 3 to about 5.

24. A process for preparing 5-aminotetrazole as defined in claim 1, wherein the acid reagent is boric acid.

25. A process for preparing 5-aminotetrazole as defined in claim 1, wherein the azide salt is sodium azide.

26. A process for preparing 5-aminotetrazole comprising the steps of:
   (a) combining cyanamide or dicyandiamide, sodium azide, and boric acid in water, wherein the combined ingredients form a reaction solution;
   (b) heating the reaction solution to about reflux temperature;
   (c) acidifying the reaction solution with a strong acid after the reaction is substantially complete, wherein the reaction solution is well agitated during said acidification step, wherein sufficient strong acid is used to lower the reaction solution's pH to a value of 3 or below, and wherein the strong acid is selected from HCl, $H_2SO_4$, $H_3PO_4$, $HNO_3$, $Cl_2CCO_2H$, $Cl_3CCO_2H$, $F_3CCO_2H$, $HCO_2H$, $HClO_4$, and mixtures thereof; and
   (d) isolating the 5-aminotetrazole product.

27. A process for preparing 5-aminotetrazole as defined in claim 26, wherein the cyanamide or dicyandiamide, the azide salt, and the acid reagent are present at approximately stoichiometric quantities.

28. A process for preparing 5-aminotetrazole as defined in claim 26, wherein the cyanamide or dicyandiamide is present at a stoichiometric excess quantity.

29. A process for preparing 5-aminotetrazole as defined in claim 26, wherein the acid reagent is present at a stoichiometric excess quantity.

30. A process for preparing 5-aminotetrazole as defined in claim 26, wherein the acidifying step is achieved by introducing the strong acid into the reaction solution.

31. A process for preparing 5-aminotetrazole as defined in claim 30, wherein the temperature of the reaction solution during the acidifying step is greater than about 0° C.

32. A process for preparing 5-aminotetrazole as defined in claim 30, wherein the reaction solution temperature during the acidifying step is at or near reflux temperature.

33. A process for preparing 5-aminotetrazole as defined in claim 30, wherein the strong acid is below room temperature.

34. A process for preparing 5-aminotetrazole as defined in claim 26, wherein the acidifying step is achieved by introducing the reaction solution into the strong acid.

35. A process for preparing 5-aminotetrazole as defined in claim 34, wherein the temperature of the reaction solution during the acidifying step is greater than about 0° C.

36. A process for preparing 5-aminotetrazole as defined in claim 34, wherein the reaction solution temperature during the acidifying step is at or near reflux temperature.

37. A process for preparing 5-aminotetrazole as defined in claim 34, wherein the strong acid is below room temperature.

38. A process for preparing a salt of 5-aminotetrazole comprising the steps of:
   (a) combining cyanamide or dicyandiamide, an azide salt, and an acid reagent in water, wherein the combined ingredients form a reaction solution;
   (b) heating the reaction solution to a temperature in the range from about 75° C. to reflux temperature;
   (c) adding to the reaction solution, a compound having a metal cation capable of forming the salt of 5-aminotetrazole and a counter ion (anion) which remains in solution after the salt of 5-aminotetrazole is formed, said adding step occurring after the reaction is substantially complete; and
   (d) isolating the salt of 5-aminotetrazole.

39. A process for preparing a salt of 5-aminotetrazole as defined in claim 38, wherein the compound having a metal cation includes a metal selected from Group Ia, Ib, IIa, IIb, IIIa, IVb, VIb, and VIII of the Periodic Table (Merck Index (9th Edition 1976)).

40. A process for preparing a salt of 5-aminotetrazole as defined in claim 38, wherein the compound having a metal cation includes a metal selected from Bi, Ca, Cd, Hg, Mo, W, Sn, Pb, Sr, Mn, Fe, Co, Ni, Cu, Zn, Tl, Pd, Pt, Cr, Ti, Ag, Au, Ba, K, Li, and Be.

41. A process for preparing 5-aminotetrazole as defined in claim 1, wherein the combining step occurs prior to the heating step.

42. A process for preparing 5-aminotetrazole as defined in claim 1, wherein the combining step occurs during the heating step.

43. A process for preparing 5-aminotetrazole as defined in claim 26, wherein the combining step occurs prior to the heating step.

44. A process for preparing 5-aminotetrazole as defined in claim 26, wherein the combining step occurs during the heating step.

45. A process for preparing a salt of 5-aminotetrazole as defined in claim 38, wherein the combining step occurs prior to the heating step.

46. A process for preparing a salt of 5-aminotetrazole as defined in claim 38, wherein the combining step during the heating step.

* * * * *